Figure 1:
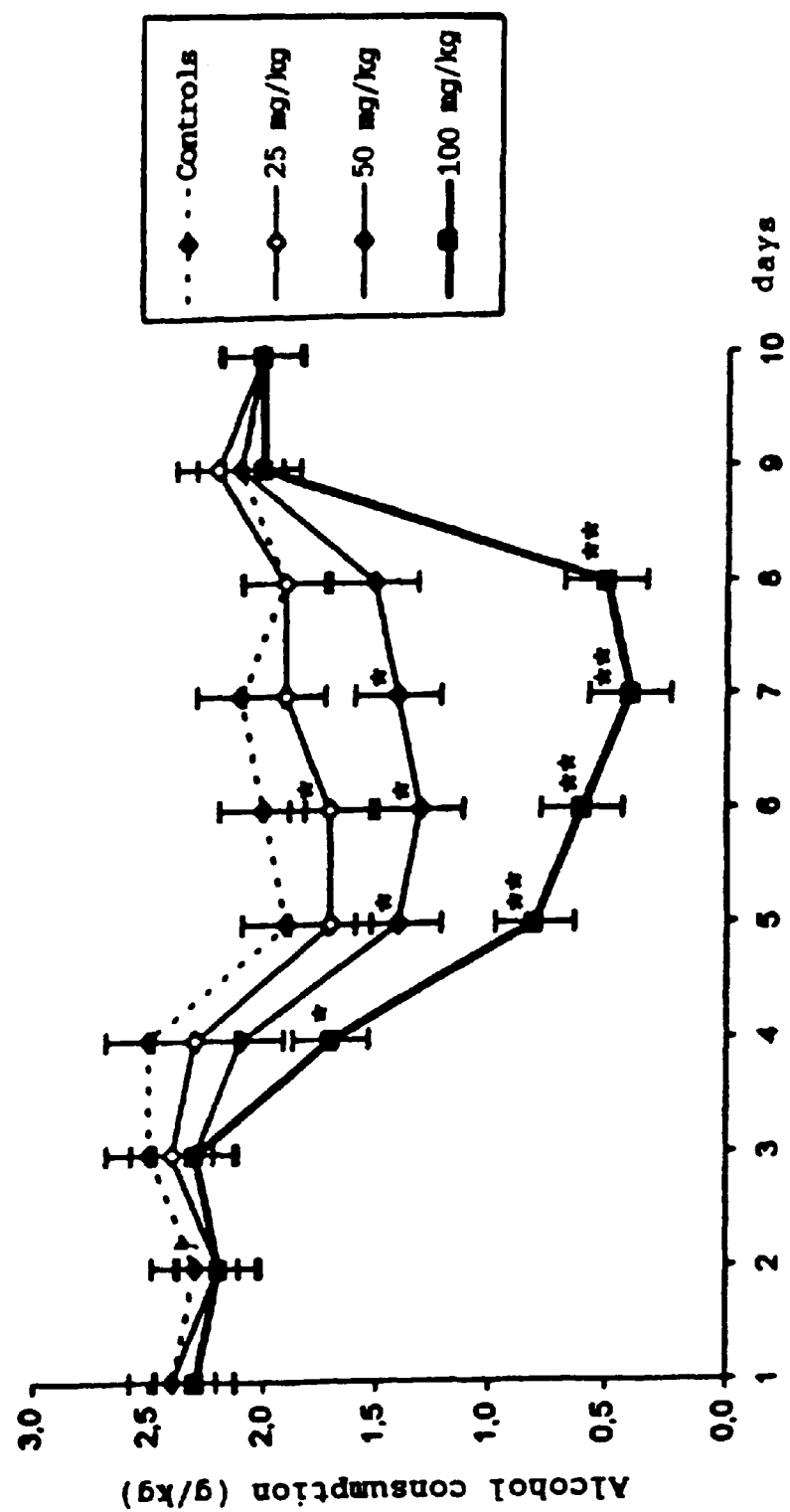

United States Patent [19]
Morazzoni et al.

[11] Patent Number: 5,904,923
[45] Date of Patent: May 18, 1999

[54] METHODS FOR PREPARING PHARMACEUTICAL COMPOSITIONS AND USING SAME TO TREAT DRUG ADDICTION

[75] Inventors: Paolo Morazzoni; Ezio Bombardelli, both of Milan, Italy

[73] Assignee: Indena S.p.A., Milan, Italy

[21] Appl. No.: 08/945,986

[22] PCT Filed: May 8, 1996

[86] PCT No.: PCT/EP96/01916

§ 371 Date: Nov. 10, 1997

§ 102(e) Date: Nov. 10, 1997

[87] PCT Pub. No.: WO96/35441

PCT Pub. Date: Nov. 14, 1996

[30] Foreign Application Priority Data

May 12, 1995 [IT] Italy .................................. MI95A0958

[51] Int. Cl.⁶ .......................... A61K 35/78; A61K 31/34; A61K 31/12
[52] U.S. Cl. ........................ 424/195.1; 514/468; 514/680
[58] Field of Search .................. 424/195.1; 514/468, 514/680

[56] References Cited

FOREIGN PATENT DOCUMENTS 0 427 026 A2   5/1991   European Pat. Off. .
0 427 026 A3   5/1991   European Pat. Off. .
WO 93/00896    1/1993   WIPO .

OTHER PUBLICATIONS

Chang et al., J. Org. Chem. 55(11), 3537–43, 1990.

"The Merck Manual of Diagnosis and Therapy", Sixteenth Edition, Merck & Co. Inc., 1992, pp. 1551–1555.

Abstract No. 86739S, "Antioxidant Activity of Quinones Extracted From Tanshen," Chemical Abstracts, vol. 117, No. 9, Aug. 31, 1992, p. 429, col. 1.

Chi–Ming Lee et al., "Miltirone, a central benzodiazepine receptor partial agonist from a Chinese medicinal herb *Salvia Miltiorrhiza*," 1991, *Neuroscience Letters*, vol. 127, pp. 237–241.

Database Napralert STN, C. P. Li, "Chinese Herbal Medicine", AN92:5003, 1974.

*Primary Examiner*—Phyllis G. Spivack
*Attorney, Agent, or Firm*—Pennie & Edmonds LLP

[57] ABSTRACT

The invention discloses to methods for preparing and using a lipophilic extract of the roots of *Salvia miltiorrhyza Bunge* for treating drug addiction. The Tanshinone IIA and Miltirone components of such lipophilic extracts are preferably used individually or in combination to treat drug addictions, and in particular, to treat alcohol addiction.

20 Claims, 4 Drawing Sheets

METHODS FOR PREPARING PHARMACEUTICAL COMPOSITIONS AND USING SAME TO TREAT DRUG ADDICTION

FIELD OF INVENTION

The present invention relates to pharmaceutical compositions for the treatment of alcohol addiction, characterized in that they contain—as the active principle—a purified lipophilic extract of *Salvia miltiorrhyza Bunge*. The invention also relates to a process for the preparation of the purified lipophilic extract of *Salvia miltiorrhyza Bunge*, and the extract thus obtained. Furthermore, the invention relates to the use of the pure active principles contained in this extract (*Tanshinone IIA* and Miltirone) in the treatment of alcohol addiction and to pharmaceutical compositions for said treatment which contain as the active principles *Tanshinone IIA* and/or Miltirone.

BACKGROUND OF INVENTION

Alcohol abuse and alcohol addiction, phenomena which can be collectively referred to by the term alcoholism, represent a serious problem for the whole of modern society (Gessa G. L., *Bisogno compulsivo di bere e "principio del piacere"* [The compulsive need to drink and the pleasure principle] in Medicina delle tossicodipendenze [Drug Addiction Medicine] II, 5 (1994)). In Italy, for example, more than 9% of the population (about 5 million people) are heavy drinkers and more than 1 million people are alcohol-addict (Calamo-Specchia F. P.—*Epidemiologia dell'alcolismo in Italia* [Epidemiology of alcoholism in Italy] in Atti del VII Congresso Nazionale della S.I.A., [Records of the 7th National Congress of the S.I.A.] Mediserve, Rome, 295–301, (1991)). These figures become much higher if we consider countries such as the United States of America where there are more than 13 million alcohol-addicts. Alcohol abuse and actual alcohol addiction result in an enormous outlay of public money (recently, since 1991, in the United States about 200 thousand million dollars a year have been spent) and are the cause of enormous social and psychological damage for the individuals involved.

The existing approaches for the treatment of alcoholism, in addition to those of a psychological nature (group therapy, etc.), consist in the use of drugs such as disulfiram and calcium carbamide which act on the metabolism of alcohol, inhibiting hepatic aldehyde-dehydrogenase and therefore raising the hematic levels of acetaldehyde, with all the undesiderable phenomena which occur each time ethanol is taken.

According to the present state of the art, the sole plant whose derivatives have been used for the treatment of alcoholism is the *Pueraria lobata* (Radix puerarie), which is widely used in traditional Chinese medicine and forms the subject of Patent Application WO 93/00896.

SUMMARY OF THE INVENTION

It has now been surprisingly found that the purified lipophilic extract of the roots of *Salvia miltiorrhyza Bunge* can be used with success for reducing the voluntary consumption of alcohol and other drugs which induce addiction. Furthermore, individual pure products isolated from the extract, such as *Tanshinone IIA* and Miltirone, have also proved to be useful. The dried roots of *Salvia miltiorrhyza Bunge* (Danshen, Radix Salviae miltiorrhyzae) are officially listed in the Chinese Pharmacopeia; they are widely used for the treatment of menstrual disturbances, cardiovascular diseases such as, for example, angina pectoris and abnormalities of platelet function, as well as insomnia (Tang, W. Eisenbrand, G., *Salvia miltiorrhyza Bge.*, in Chinese drugs of plant origin; Chemistry, Pharmacology, and Use in Traditional Chinese Medicine, pp. 891–902—Springer-verlag, Berlin (1992); Kee Chang Huang, *Antianginal Herbs* in The Pharmacology of Chinese Herbs, pp.81–84—CRC Press, Boca Raton (1993)).

The use of hydro-alcoholic extracts of *Salvia miltiorrhyza* for the topical treatment of excess fat deposits is also known (Italian Patent 1,239,281).

DESCRIPTION OF THE INVENTION

The extract according to the invention, unlike that which is known, is of the lipophilic type and is obtained by extraction of the roots of *Salvia miltiorrhyza* with acetone, at temperatures of between about 20 and 50° C., using a drug/solvent ratio (w/v) of between 1:2 and 1:10, preferably about 1:5. Following concentration down to about 1/20th to 1/50th of the initial volume, water and a solvent which is immiscible in water are added. The acetone is removed by means of repeated washings with water while the organic phase containing the active principles is concentrated, following dilution, where necessary, with 95° ethanol.

The lipophilic extract according to the present invention is characterized by having a content of from 5 to 30% w/w, preferably from 15 to 25%, of Tanshinone IIA and of from 0.5 to 3% w/w, preferably of from 0.8 to 2%, of Miltirone.

Determination of the inhibiting action on alcohol consumption was performed using alcohol-consuming rats of the strain called "Sardinian alcohol-preferring" (Sp) (Fadda F., Mosca E., Colombo G., Gessa G. L., *Alcohol-Preferring rats: Genetic sensitivity to alcohol-induced stimulation of dopamine metabolism*, in Physiol. Behav. 47, 727 (1990)).

These animals, which given a free choice between alcohol and water consume daily 6 to 7 g of alcohol per kg of body weight (with a water-to-alcohol ratio higher than 2:1), during the last few years have been used with success to determine the effect of various substances on the voluntary consumption of alcohol; see, for example, Balakleevsky A., Colombo G., Fadda F., Gessa G. L., *Ro 19-4603, a benzodiazepine receptor inverse agonist, attenuates voluntary ethanol consumption in rats selectively bred for high ethanol preference*, in Alcohol Alcohol. 25, 449–452 (1990); Fadda F., Garau B., Colombo G., Gessa G. L., *Isradipine and other calcium channel antagonists attenuate ethanol consumption in ethanol-preferring rats*, in Alcoholism: Clinical and Experimental Research 16(3), 449–452 (1992).

The animals, which were kept under normal housing conditions, were given a free choice between water (which was always present) and alcohol (a 10% solution v/v) which was offered for a period of 4 hours a day (i.e. the first 4 hours of darkness during the day/night cycle). The amounts of water and alcohol consumed were recorded every day at the same time. Food was offered ad libitum. Once a stable consumption of alcohol and water was reached, different doses of purified lipophilic extract of *Salvia miltiorrhyza* (prepared as above) dissolved in dimethylsulfoxide, were administered orally in a volume amount of 2 ml/kg once a day for 5 consecutive days. An equal volume of the carrier was used as the control. At the end of treatment, the alcohol and water consumption was recorded until the values recorded prior to the treatment were reestablished. Statistical significant difference from the mean of the values obtained in the group treated with the carrier alone (* $p<0.05$, ** $p<0.01$) was evaluated by the Dunnet test for multiple comparisons.

Figure 2:
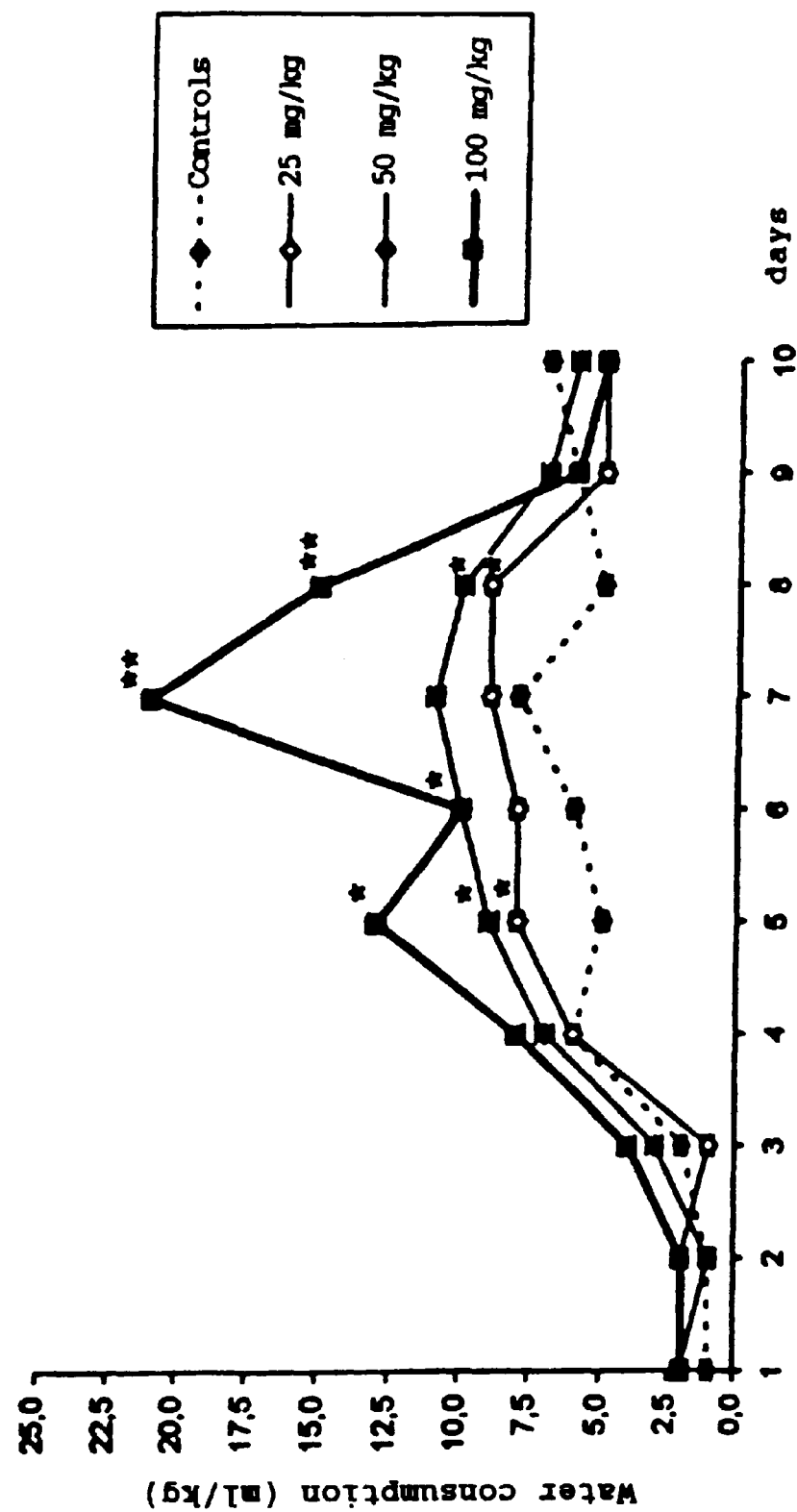
Figure 3:
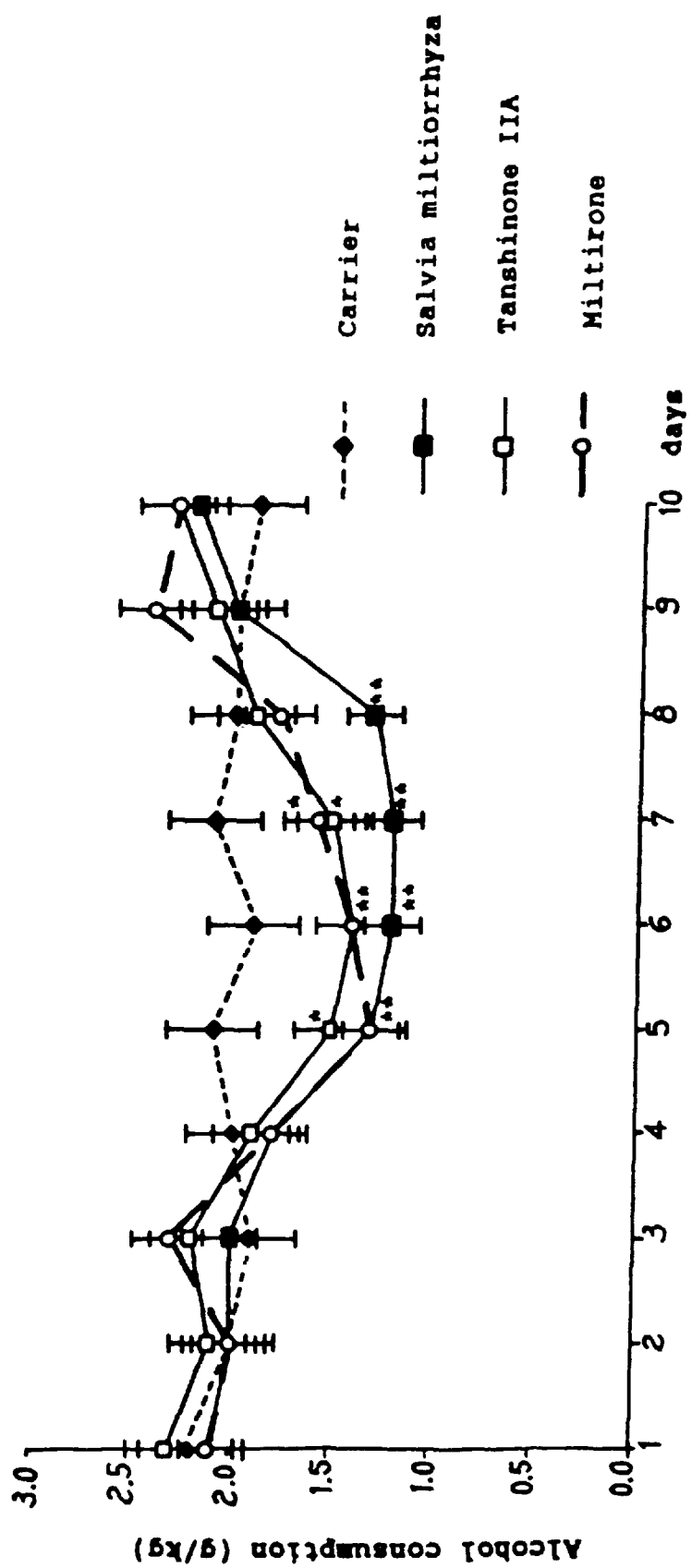
Figure 4:
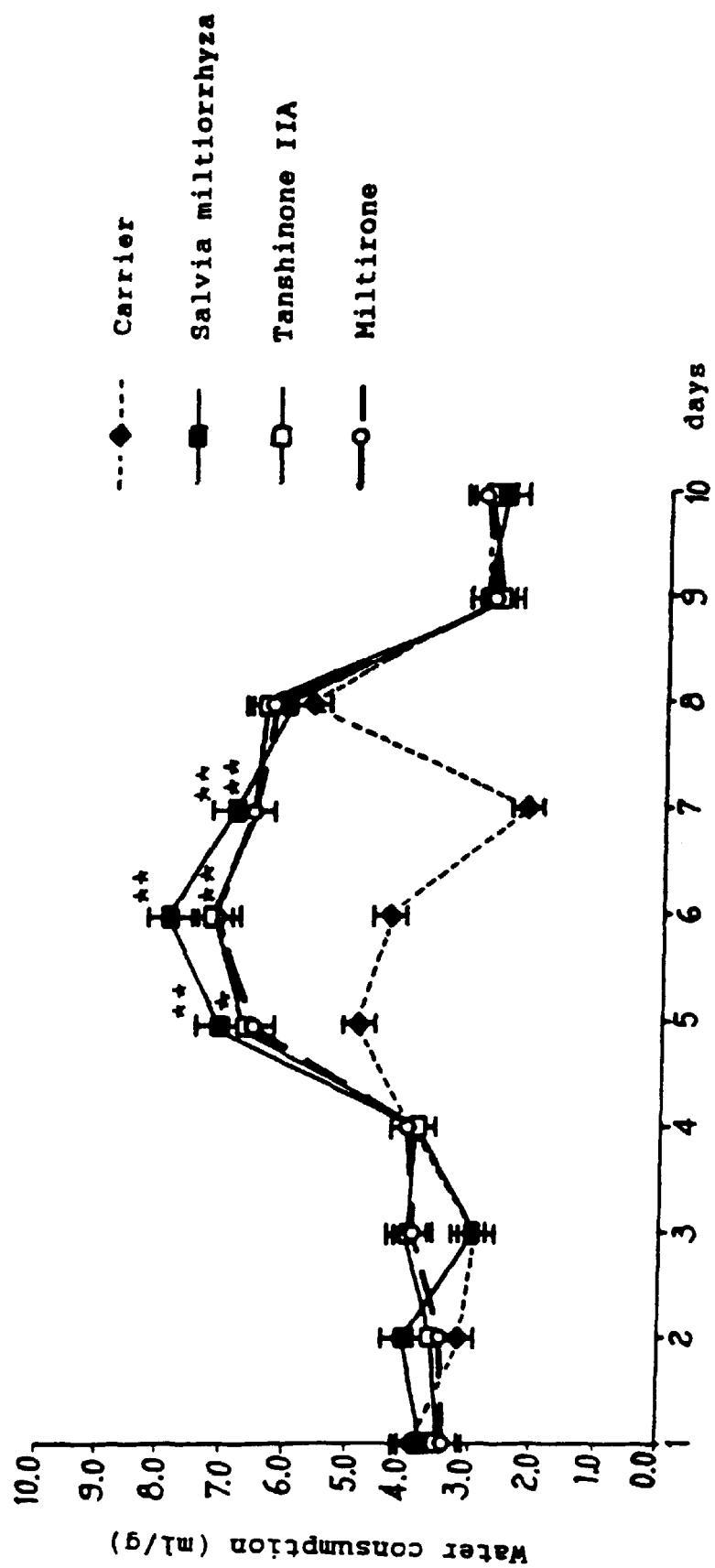

FIG. 1 shows the effect of repeated oral administration of increasing doses of the extract on alcohol consumption; FIG. 2 shows the effect of increasing doses on water consumption. FIG. 3, on the other hand, shows the effect on alcohol consumption resulting from repeated doses both of the extract and of the principles contained therein (*Tanshinone IIA* and Miltirone); FIG. 4, finally, illustrates the effect on water consumption of the extract and the said principles when administered in repeated doses.

From an examination of FIGS. 1 and 2 it can be concluded that the extract reduces alcohol consumption significantly and in a dose-related manner, this result being achieved in some cases (i.e. with the highest dose) already after the first day of administration. The reduction in alcohol consumption remains constant until the fifth day and then regresses following suspension of the treatment. Moreover, it is surprising to note that this trend is accompanied by the tendency for a gradual increase in the water consumption, as if the animal were substituting it for the alcohol. This latter observation is of particular importance since it shows that the treatment carried out with the product being tested is perfectly well-tolerated and the animal returns without any difficulty to a more physiological life cycle, using water instead of alcohol.

The administration in constant doses, repeated for 5 days, of both the extract and *Tanshinone IIA* and Miltirone (FIGS. 3 and 4) confirms the results indicated above, but demonstrates that the pure components—taking account of the doses—are the main factors responsible for the effect of the extract.

The invention therefore provides pharmaceutical compositions which can be administered orally and which contain as the active principle either the lipophilic extract of *Salvia miltiorrhyza* or the purified active principles *Tanshinone IIA* and/or Miltirone, the latter being obtainable from commercial sources or by means of conventional purification of the lipophilic extract. The compositions of the invention, in addition to conventional excipients or carriers, will contain from about 10 to about 500 mg of the extract or the equivalent doses of *Tanshinone IIA* and Miltirone, taking into account their extract content.

EXAMPLES

Example 1

Preparation of the Lipophilic Extract 1 kg of finely ground roots of *Salvia miltiorrhyza* are extracted 4 times using 5 l of acetone at 50° C. The recombined extracts are concentrated under a vacuum to 500 ml; the concentrate is diluted with 1 l of methylene chloride and 500 ml of $H_2O$. The phases are separated and the organic phase containing the active principles is washed with water until the acetone and the unwanted polar substances are eliminated.

The chloromethylene phase is concentrated to a small volume; the residue is diluted with 300 ml of 95° ethanol. The solution is concentrated under a vacuum to dryness at a temperature of 60° C. After drying overnight, 11.3 g of extract are obtained, containing 15.2% of *Tanshinone IIA* and 1.1% of Miltirone.

Example 2

Formulation in Capsule Form

| Each 130 mg capsule contains: | |
| --- | --- |
| Extract of Example 1 | 25 mg |
| Pregelatinized starch | 25 mg |
| Microcrystalline cellulose | 49 mg |
| Lactose | 15 mg |
| Colloidal silica | 6 mg |
| Cross-linked sodium carboxymethylcellulose | 6.5 mg |
| Polyvinylpyrrolidone | 2.5 mg |
| Magnesium stearate | 1 mg |

Example 3

Formulation in Tablet Form

| Each 400 mg tablet contains: | |
| --- | --- |
| Extract of Example 1 | 100 mg |
| Pregelatinized starch | 100 mg |
| Microcrystalline cellulose | 96 mg |
| Lactose | 45 mg |
| Colloidal silica | 25 mg |
| Cross-linked sodium carboxymethylcellulose | 20 mg |
| Polyvinylpyrrolidone | 10 mg |
| Magnesium stearate | 4 mg |

What is claimed is:

1. A method for the treatment of drug addiction which comprises administering to a person in need of such treatment a therapeutically effective amount of lipophilic extract from the roots of *Salvia miltiorrhyza Bunge* plant.

2. The method of claim 1, wherein the lipophilic extract includes Tanshinone IIA.

3. The method of claim 2, which further comprises providing the Tanshinone IIA in an amount from 15% to 25% by weight of the lipophilic extract.

4. The method of claim 1, wherein the lipophilic extract includes Miltirone.

5. The method of claim 4, which further comprises providing the Miltirone in an amount from 0.8% to 2% by weight of the lipophilic extract.

6. The method of claim 1, wherein the lipophilic extract includes a mixture of Tanshinone IIA and Miltirone.

7. The method of claim 6, wherein the lipophilic extract includes from 5% to 30% by weight Tanshinone IIA and of 0.5% to 3% by weight Miltirone.

8. The method of claim 6, which further comprises providing the Tanshinone IIA in an amount from 15% to 25% by weight and providing the Miltirone in an amount from 0.8% to 2% by weight of the lipophilic extract.

9. A method for preparing the lipophilic extract of claim 1, which comprises:

extracting the roots of *Salvia miltiorrhyza* with acetone to form an extraction;

concentrating the extraction to form a concentrate;

treating the concentrate with water and a water-immiscible solvent; and removing the acetone from the concentrate to yield the lipophilic extract.

10. The method of claim 9, further comprising purifying the lipophilic extract.

11. The method of claim 9, wherein the extracting step is maintained at a temperature between about 20° C. to 50° C.

12. The method of claim 9, wherein the concentrate is about 1/20 to 1/50 of the initial volume of the extraction.

13. A method for the treatment of alcohol addiction which comprises administering to a person in need of such treatment a therapeutically effective amount of lipophilic extract from the roots of *Salvia miltiorrhyza Bunge* plant.

14. The method of claim 13, wherein the lipophilic extract includes Tanshinone IIA.

15. The method of claim 14, which further comprises providing the Tanshinone IIA in an amount from 15% to 25% by weight of the lipophilic extract.

16. The method of claim 13, wherein the lipophilic extract includes Miltirone.

17. The method of claim 16, which further comprises providing the Miltirone in an amount from 0.8% to 2% by weight of the lipophilic extract.

18. The method of claim 13, wherein the lipophilic extract includes a mixture of Tanshinone IIA and Miltirone.

19. The method of claim 18, wherein the lipophilic extract includes from 5% to 30% by weight Tanshinone IIA and of 0.5% to 3% by weight Miltirone.

20. The method of claim 18, which further comprises providing the Tanshinone IIA in an amount from 15% to 25% by weight and providing the Miltirone in an amount from 0.8% to 2% by weight of the lipophilic extract.

* * * * *